US012642879B2

(12) United States Patent
Pai et al.

(10) Patent No.: US 12,642,879 B2
(45) Date of Patent: *Jun. 2, 2026

(54) METHOD AND SYSTEM OF CONTROLLING A COHORT OF OZONE GAS GENERATING DEVICES

(71) Applicant: 13482073 CANADA INC., Markham (CA)

(72) Inventors: Ching Kuo Pai, Markham (CA); Peter Birch, Markham (CA)

( * ) Notice: Subject to any disclaimer, the term of this patent is extended or adjusted under 35 U.S.C. 154(b) by 955 days.

This patent is subject to a terminal disclaimer.

(21) Appl. No.: 17/718,404

(22) Filed: Apr. 12, 2022

(65) Prior Publication Data

US 2023/0293753 A1     Sep. 21, 2023

Related U.S. Application Data

(63) Continuation-in-part of application No. 17/699,488, filed on Mar. 21, 2022.

(51) Int. Cl.
| | |
|---|---|
| *A61L 2/24* | (2006.01) |
| *A61L 2/202* | (2026.01) |
| *A61L 9/015* | (2006.01) |
| *C01B 13/10* | (2006.01) |
| *G01N 33/00* | (2006.01) |

(52) U.S. Cl.
CPC ................. *A61L 2/24* (2013.01); *A61L 2/202* (2013.01); *A61L 9/015* (2013.01); *C01B 13/10* (2013.01); *G01N 33/0075* (2013.01); *A61L 2202/11* (2013.01); *A61L 2202/14* (2013.01); *A61L 2209/12* (2013.01)

(58) Field of Classification Search
CPC ... A61L 2/00; A61L 2/20; A61L 2/202; A61L 2/24; A61L 9/00; A61L 9/015; A61L 2202/00; A61L 2202/10; A61L 2202/11; A61L 2202/14; A61L 2209/00; A61L 2209/10; A61L 2209/12; C01B 13/00; C01B 13/10; C01B 2201/00; C01B 2201/80; C01B 2201/82; C01B 2201/90; G01N 33/00; G01N 33/0004; G01N 33/0009; G01N 33/0073; G01N 33/0075
See application file for complete search history.

(56) References Cited

U.S. PATENT DOCUMENTS

| | | | | |
|---|---|---|---|---|
| 11,274,053 B1* | 3/2022 | Lynn | ..................... | A61L 2/183 |
| 2009/0185959 A1* | 7/2009 | Weber | ..................... | A61L 9/22 |
| | | | | 422/107 |
| 2024/0157014 A1* | 5/2024 | Birch | .................. | G08B 21/182 |

* cited by examiner

*Primary Examiner* — Natasha E Young

(57) ABSTRACT

A method and system of controlling a cohort of ozone gas generating devices. The method comprises identifying, at a computing device, a plurality of ozone gas generating devices that constitute the cohort, detecting, via at least one remote ozone gas sensor device located in a spatial area associated with the cohort in conjunction with one or more processors of the computing device, a concentration of ozone gas constituent of ambient air within the spatial area, and instructing, responsive to detecting the concentration of the ozone gas constituent as being one of above and below a predetermined threshold concentration, at least one ozone gas generating device of the cohort to perform one of increasing and decreasing a rate of ozone gas generation associated therewith.

20 Claims, 9 Drawing Sheets

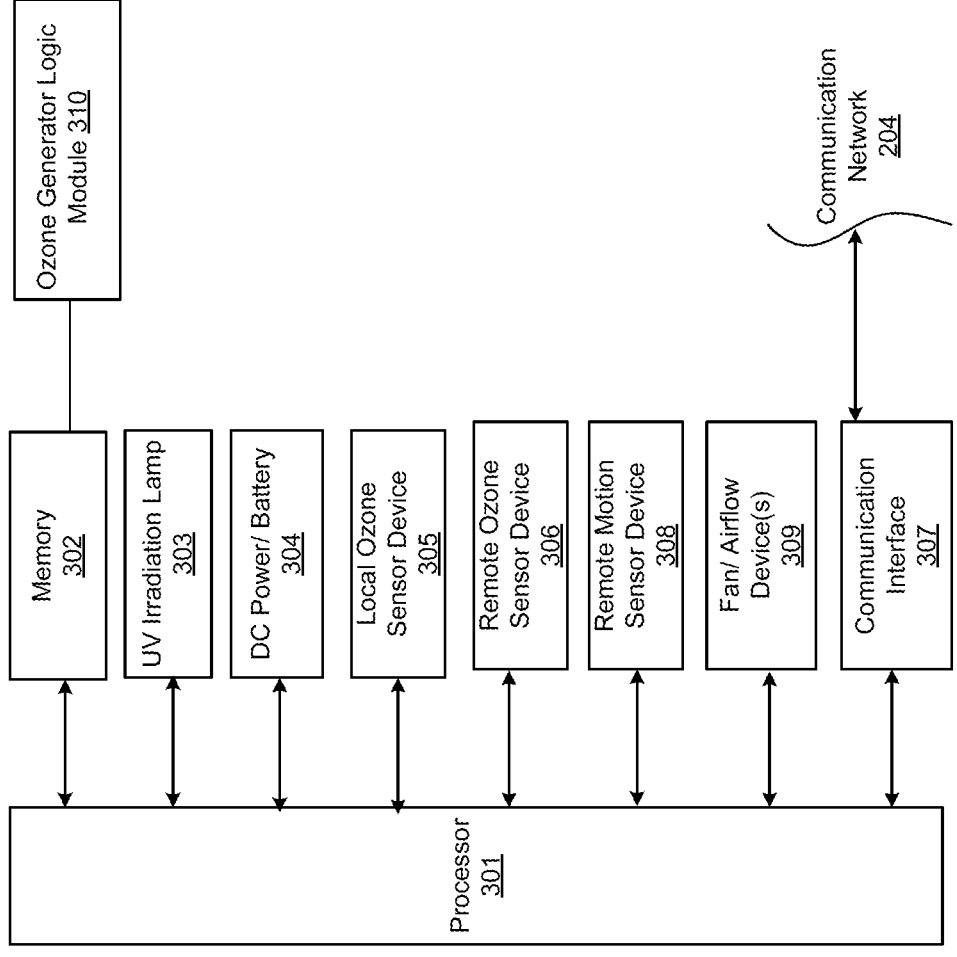
FIG. 3

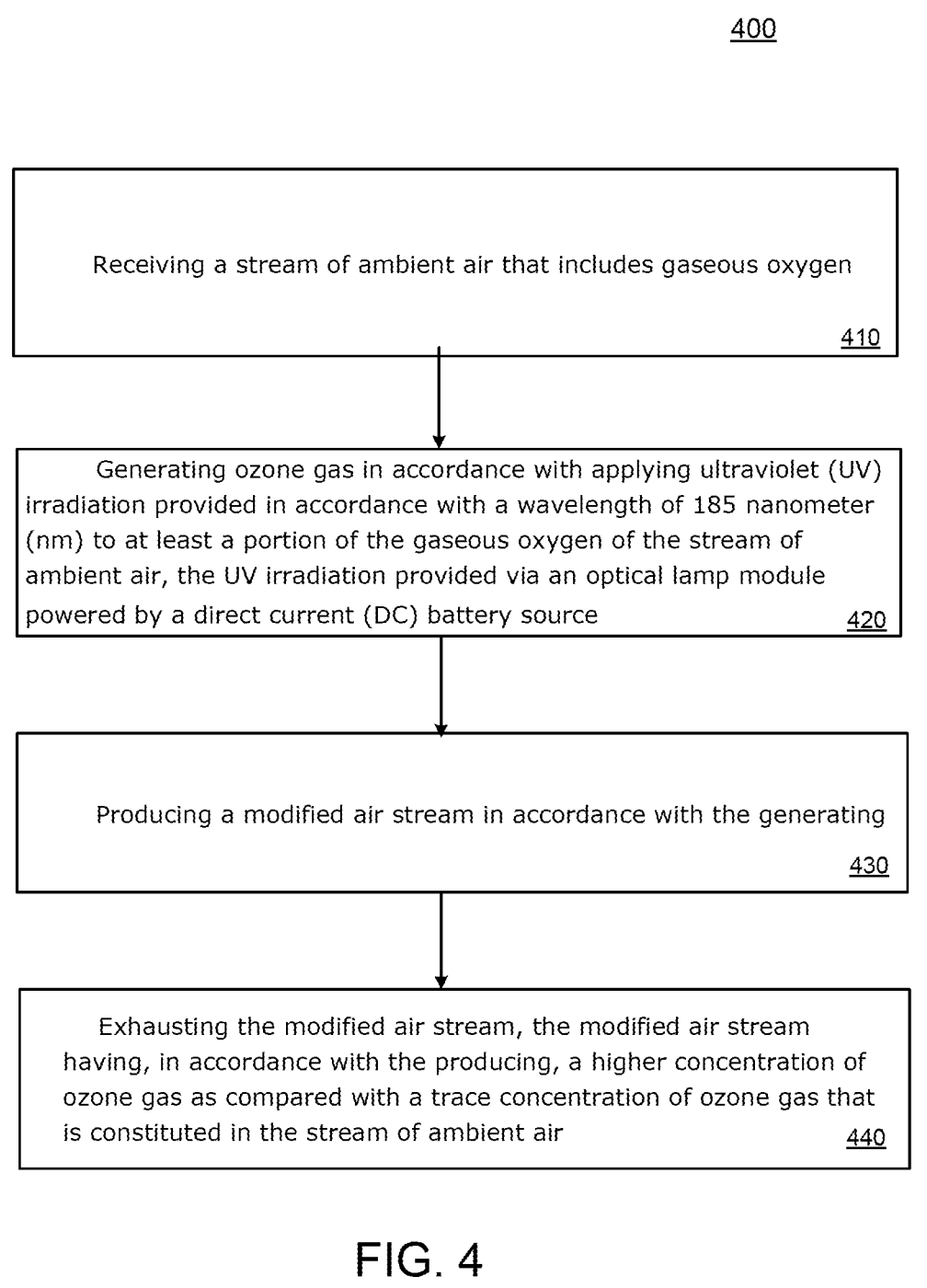

400

Receiving a stream of ambient air that includes gaseous oxygen

410

Generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source          420

Producing a modified air stream in accordance with the generating

430

Exhausting the modified air stream, the modified air stream having, in accordance with the producing, a higher concentration of ozone gas as compared with a trace concentration of ozone gas that is constituted in the stream of ambient air          440

FIG. 4

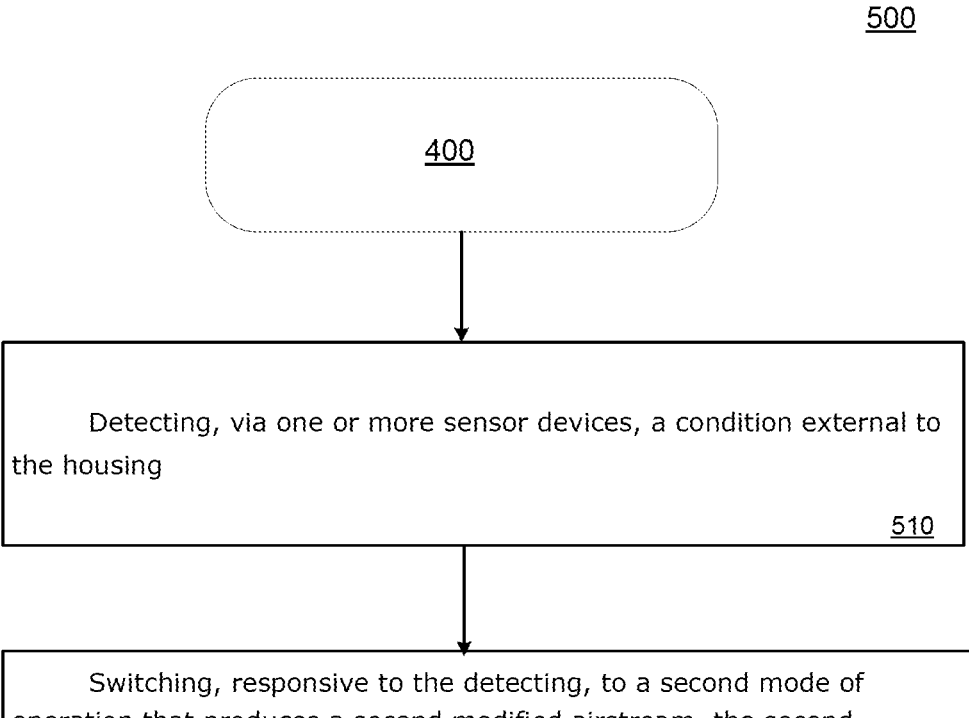

500

400

Detecting, via one or more sensor devices, a condition external to the housing

510

Switching, responsive to the detecting, to a second mode of operation that produces a second modified airstream, the second modified airstream comprising at least one of: (i) a higher concentration of ozone gas than the first modified airstream, and (ii) a higher flowrate of the exhausting as compared with the first modified airstream          520

Figure 7:
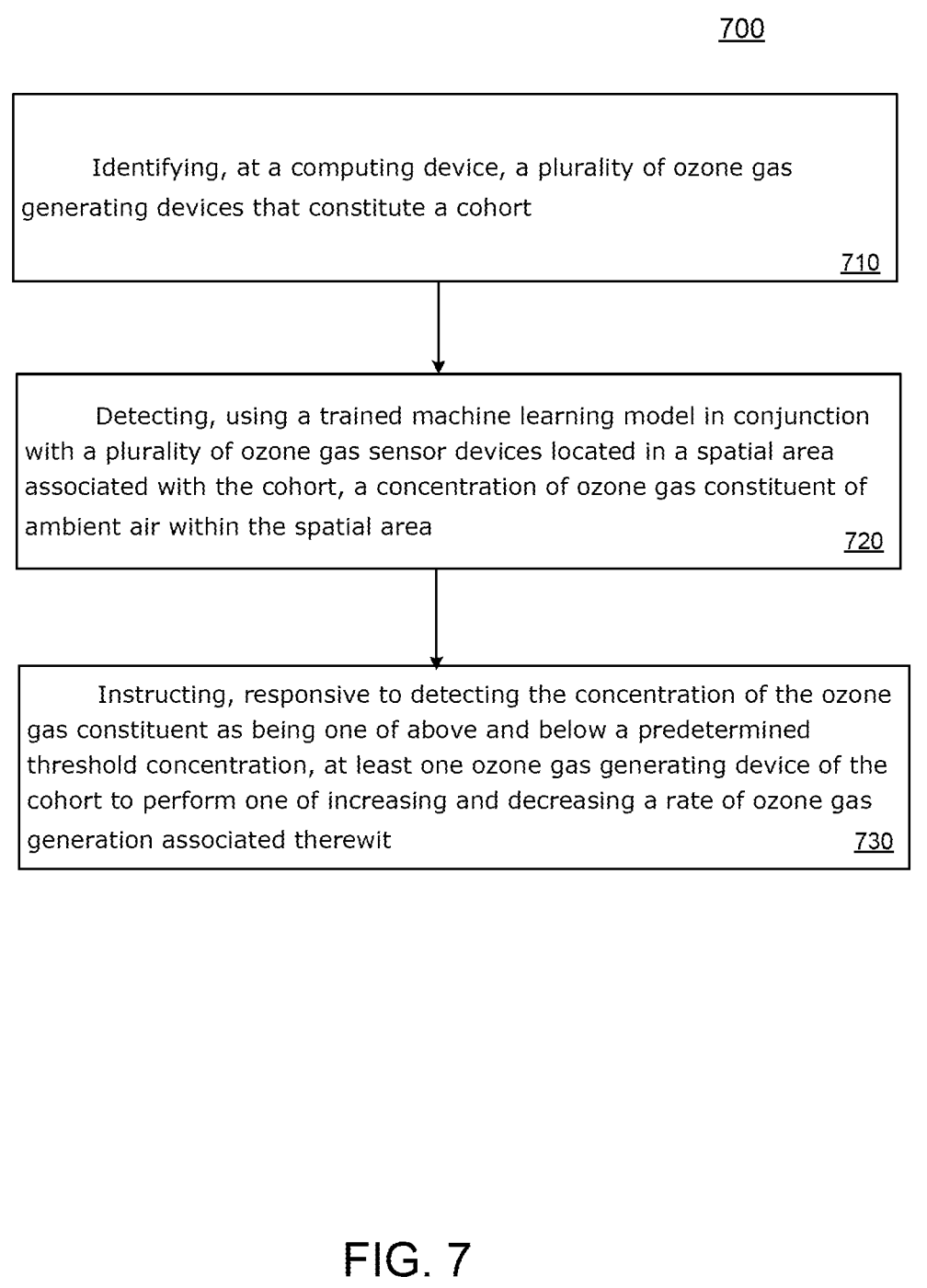

Identifying, at a computing device, a plurality of ozone gas generating devices that constitute a cohort

710

Detecting, using a trained machine learning model in conjunction with a plurality of ozone gas sensor devices located in a spatial area associated with the cohort, a concentration of ozone gas constituent of ambient air within the spatial area          720

Instructing, responsive to detecting the concentration of the ozone gas constituent as being one of above and below a predetermined threshold concentration, at least one ozone gas generating device of the cohort to perform one of increasing and decreasing a rate of ozone gas generation associated therewit          730

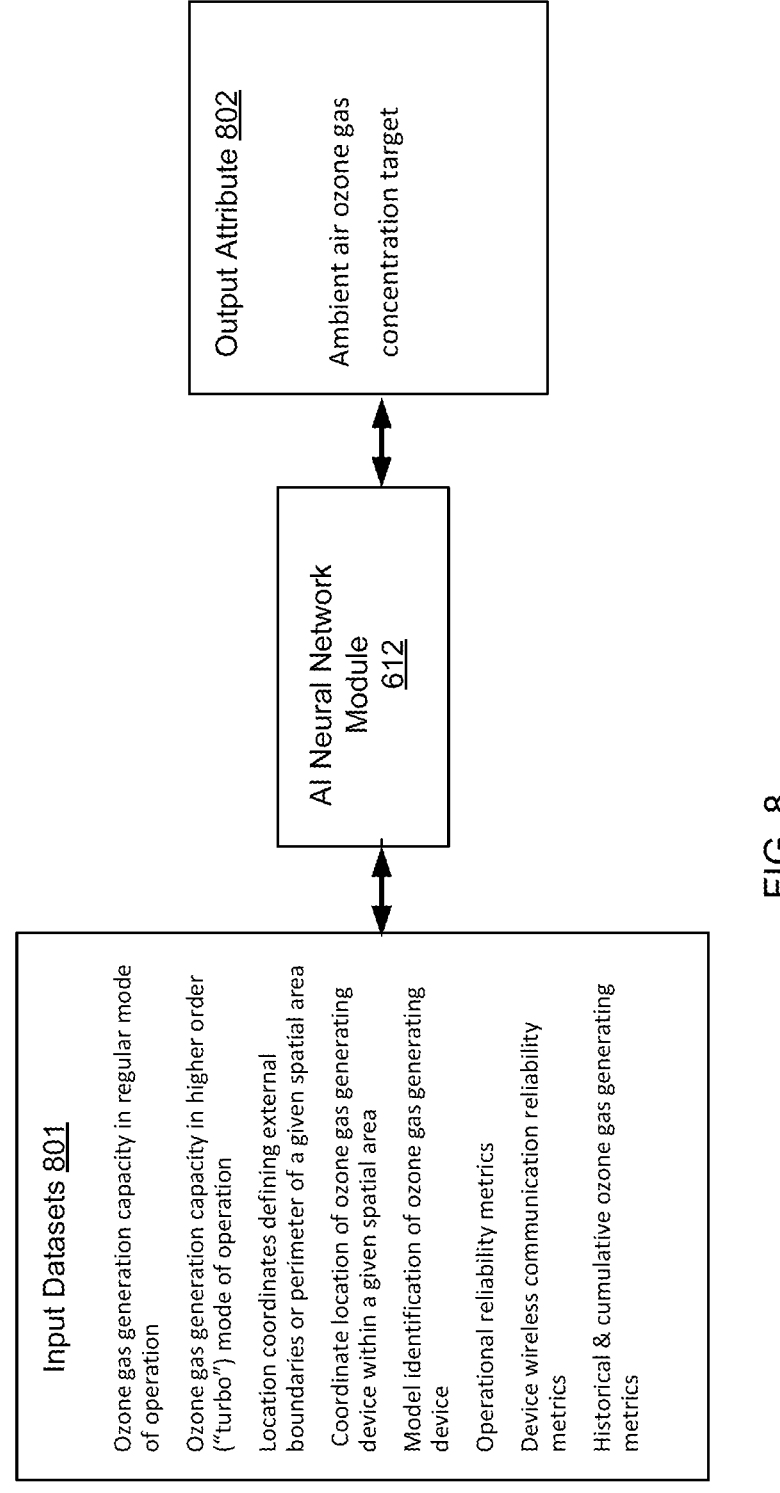

Output Attribute 802

Ambient air ozone gas concentration target

AI Neural Network Module 612

Input Datasets 801

Ozone gas generation capacity in regular mode of operation

Ozone gas generation capacity in higher order ("turbo") mode of operation

Location coordinates defining external boundaries or perimeter of a given spatial area Coordinate location of ozone gas generating device within a given spatial area Model identification of ozone gas generating device Operational reliability metrics Device wireless communication reliability metrics Historical & cumulative ozone gas generating metrics

Figure 9:
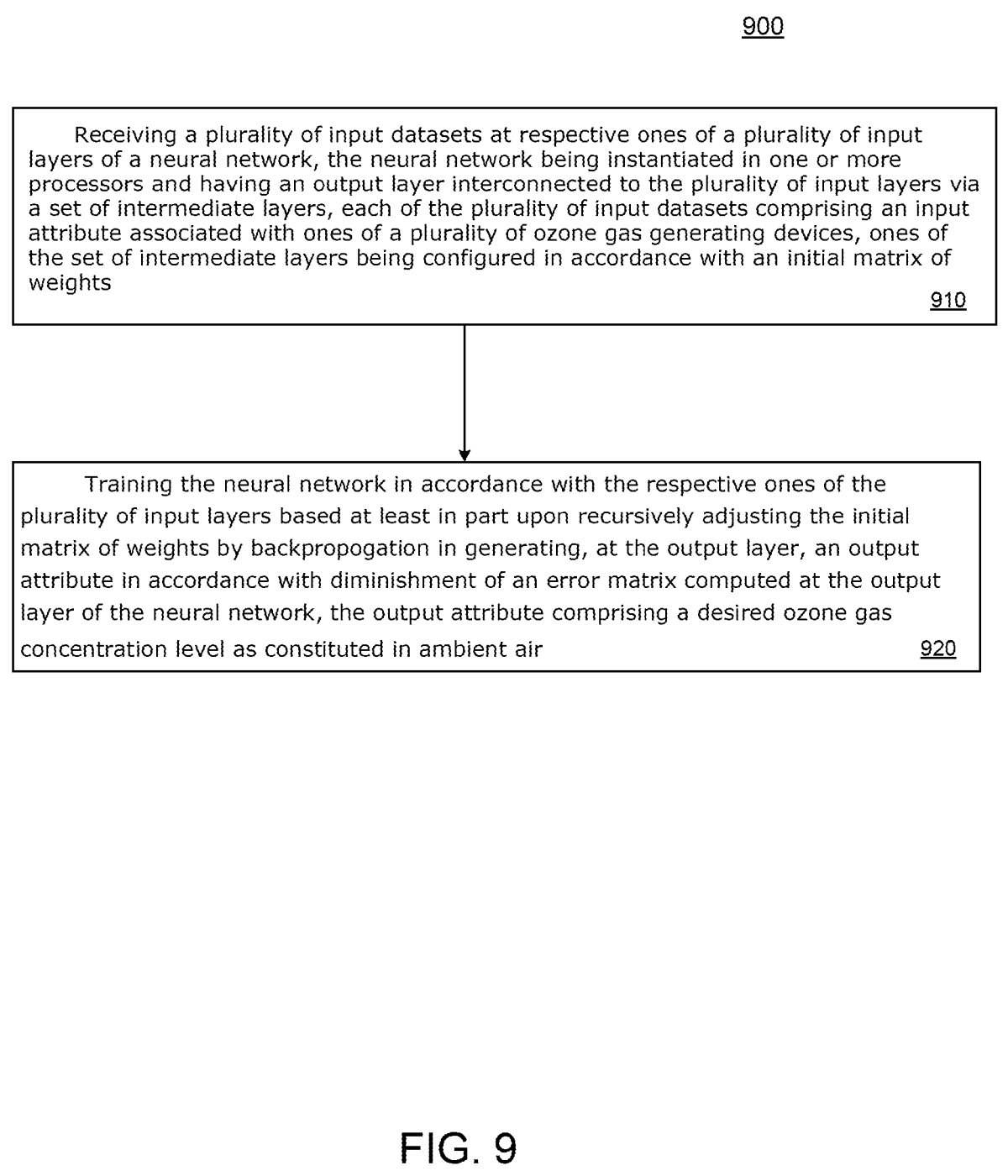

Receiving a plurality of input datasets at respective ones of a plurality of input layers of a neural network, the neural network being instantiated in one or more processors and having an output layer interconnected to the plurality of input layers via a set of intermediate layers, each of the plurality of input datasets comprising an input attribute associated with ones of a plurality of ozone gas generating devices, ones of the set of intermediate layers being configured in accordance with an initial matrix of weights

910

Training the neural network in accordance with the respective ones of the plurality of input layers based at least in part upon recursively adjusting the initial matrix of weights by backpropogation in generating, at the output layer, an output attribute in accordance with diminishment of an error matrix computed at the output layer of the neural network, the output attribute comprising a desired ozone gas concentration level as constituted in ambient air

METHOD AND SYSTEM OF CONTROLLING A COHORT OF OZONE GAS GENERATING DEVICES

RELATED APPLICATION

This application is a continuation-in-part of, and claims the benefit of priority to, U.S. patent application Ser. No. 17/699,488 filed on Mar. 21, 2022; said U.S. patent application Ser. No. 17/699,488 is incorporated by reference herein in its entirety.

TECHNICAL FIELD

The disclosure herein relates to controlling ozone gas generating devices, including cloud-based control thereof.

BACKGROUND

Ozone, a trace gas in the earth's atmosphere, is formed by molecules made up of 3 oxygen atoms ($O_3$) and has the characteristic of being a powerful oxidizing agent proven to be highly effective in killing bacteria, fungi and molds and inactivating viruses. Ozone can be used for the treatment of potentially contaminated surfaces, water, and ambient air thanks to its powerful germicidal effect on a wide spectrum of microorganisms. Ozone created by various kinds of ozone generators can reach every corner of the environment of a single room or a larger space, without leaving any undesired residues. The effectiveness of ozone in treating microorganisms, especially bacteria and viruses is related to various factors, such as ozone concentration, the temperature of the environment, humidity of the environment and exposure time.

BRIEF DESCRIPTION OF THE DRAWINGS

FIG. 3 illustrates, in an example embodiment, an example architecture of an ozone gas generating device deployed in an ozone generating system.

FIG. 4 illustrates, in an example embodiment, a method of operation of an ozone generating device.

FIG. 5 illustrates, in yet another example embodiment, a method of operation of an ozone generating device in accordance with a higher order method of operation.

FIG. 7 illustrates, in an example embodiment, a method of controlling a cohort of ozone gas generating devices that incorporates an artificial intelligence machine learning-based system.

FIG. 8 illustrates, in an example embodiment, input datasets and output attribute of an artificial intelligence machine learning-based system for controlling a cohort of ozone gas generating device.

FIG. 9 illustrates, in one embodiment, a method of training an artificial intelligence machine learning-based system in controlling a cohort of ozone gas generating devices.

DETAILED DESCRIPTION

Figure 1:
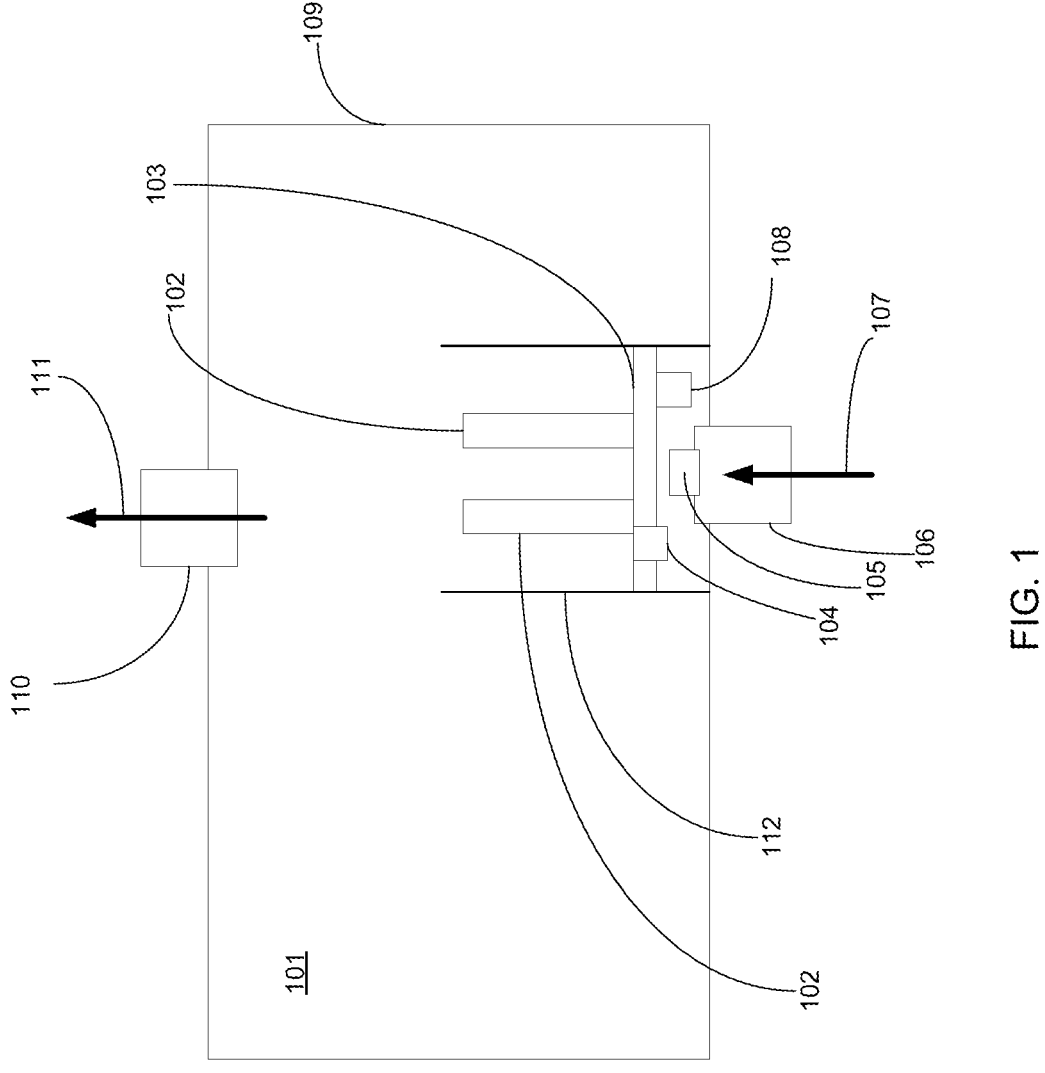
FIG. 1 illustrates, in an example embodiment, an ozone gas generating device.

Embodiments herein recognize the need for advantageously leveraging the anti-viral and anti-microbial attributes of ozone gas within an at least partially closed environment of living space, while controlling ozone gas concentration within acceptable levels in order to avoid adverse effects on human beings and other living creatures. Embodiments herein also recognize the need for ozone gas generators to operationally ramp up and swiftly attain desired ozone gas concentrations in the given living space, yet without compromising safety of any beings occupying that living space. In particular, embodiments herein provide for an ozone gas generating device capable of operating in both a regular mode of operation as well as a higher order mode of operation as characterized by increased rate of generation of ozone gas, somewhat analogous to a "turbocharged" mode of operation, but only upon ascertaining or sensing that it would be safe to do so, thus avoiding unduly high and unsafe high concentration levels that could adversely affect living beings currently occupying an at least partially enclosed room or similar living space.

Provided is a method of generating ozone gas. The method comprises receiving a stream of ambient air that includes gaseous oxygen, generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source, producing a modified air stream in accordance with the generating and exhausting the modified air stream, the modified air stream having, in accordance with the producing, a higher concentration of ozone gas as compared with a trace concentration of ozone gas that is constituted in the stream of ambient air. In one embodiment having a heightened safety protocol, a remote motion sensor device can be used to detect that no human persons or living creatures are active within the surroundings, such as an enclosed room in which the ozone gas generating device is located, before switching to the second mode of operation having increased rate of generation or production of ozone gas. A second modified airstream generated in this higher order, or "turbocharged", mode of operation can comprise a higher concentration of ozone gas than the first modified airstream, and optionally generated with a higher flowrate of exhausting as compared with the first modified airstream. In this manner, a higher rate of production of ozone gas can be generated within a given time period for dissemination into the surroundings safely while avoiding potentially adverse effects on living occupants in the space.

Also provided is an ozone gas generating system comprising a processor and a non-transitory memory including instructions. The instructions when executed by the processor causes the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air. The UV irradiation is provided via an optical lamp module powered by a direct current (DC) battery source. Generating the ozone gas produces a modified air stream constituted of ozone-rich air which has a higher concentration of ozone gas as compared with a trace concentration of ozone gas that is constituted in the stream of ambient air and is exhausted via exhaust port 110 to the surroundings.

Embodiments herein further recognize that when multiple ones of ozone gas generating devices are portable and individually deployed in operation within a given spatial area, a need exists to ensure that the overall attendant effect, in terms of ozone gas concentration within the spatial area, is optimized for human safety while advantageously leveraging anti-viral and anti-microbial attributes. Embodiments herein further provide methods and systems for optimized control of a cohort of ozone gas generating devices using, at least in part via wireless coupling, communication with a computing device, by treating the cohort of devices in attendance at any given time as an ad hoc ozone gas generating network of devices. In this manner, individual ones of the portable ozone gas generating devices can freely join or leave the ad hoc network as their physical location transitions into, or out of, a given spatial area. In embodiments, such a network of ozone gas generating devices can be subjected to control using an artificial intelligence or machine learning neural network model, once that model is appropriately trained. In some embodiments, the control scheme can be implemented via a cloud-based server computing device, with individual ozone gas generating devices considered as respective Internet of Things (IoT) nodes within a given ad hoc network.

Further provided is a method of controlling a cohort of ozone gas generating devices. The method comprises identifying, at a computing device, a plurality of ozone gas generating devices that constitute the cohort, detecting, via at least one ozone gas sensor device located in a spatial area associated with the cohort in conjunction with one or more processors of the computing device, a concentration of ozone gas constituent of ambient air within the spatial area, and instructing, using the one or more processors responsive to detecting the concentration of the ozone gas constituent as being one of above and below a predetermined threshold concentration, at least one ozone gas generating device of the cohort to perform one of increasing and decreasing a rate of ozone gas generation associated therewith. In embodiments wherein a plurality of ozone gas sensor devices are located within the spatial area associated with the cohort, the method further includes detecting the concentration of ozone gas constituent of ambient air at least partly using a trained machine learning model in conjunction with the plurality of ozone gas sensor devices.

Also provided is a computing device, which in one embodiment may be a server computing device. The computing device includes a processor and a non-transitory memory including instructions. The instructions when executed by the processor cause the processor to perform operations comprising identifying, at a computing device, a plurality of ozone gas generating devices that constitute a cohort, detecting, via at least one ozone gas sensor device located in a spatial area associated with the cohort in conjunction with one or more processors of the computing device, a concentration of ozone gas constituent of ambient air within the spatial area, and instructing, using the one or more processors responsive to detecting the concentration of the ozone gas constituent as being one of above and below a predetermined threshold concentration, at least one ozone gas generating device of the cohort to perform one of increasing and decreasing a rate of ozone gas generation associated therewith. In embodiments wherein a plurality of ozone gas sensor devices are located within the spatial area associated with the cohort, and the instructions are further executable to detect the concentration of ozone gas constituent of ambient air at least partly using a trained machine learning model in conjunction with the plurality of ozone gas sensor devices.

Embodiments described herein can be implemented using programmatic modules, through the use of instructions that are executable by one or more processors. A programmatic module can include a program, a sub-routine, a portion of a program, or a software component or a hardware component capable of performing one or more stated tasks or functions. As used herein, a programmatic module can exist on a hardware component independently of other modules or components, or can be a shared element of other modules, programs or machines.

One or more embodiments described herein provide that methods, techniques, and actions performed in an ozone generating device and system are performed programmatically, or as a computer-implemented method. Programmatically, as used herein, means through the use of code or computer-executable instructions. These instructions can be stored in one or more memory resources accessible to the ozone gas generating device.

FIG. 1 illustrates, in a diagrammatic representation not necessarily depicted to scale, an embodiment of ozone gas generating device 101 (variously referred to herein also as "ozone generating device 101"). In one embodiment, ozone generating device 101 includes housing 109 having ingress port 106 for ambient air stream 107 and exhaust port 110 for egress of ozone-rich air stream 111. Controller module 103 may be manifested in a printed circuit board facilitating electronic interconnection with one or more optically irradiating lamps 102 providing ultraviolet irradiation in a wavelength of 185 nanometers (nm), with direct current (DC) battery 104 providing an electrical power source and being at least partly enclosed within protective cylindrical enclosure 112. In embodiments, ozone generating device 101 operates at substantially constant-voltage as provided by DC battery 104. Local ozone gas concentration sensor 108 may be electrically interconnected to controller module 103. One or more airflow pressure differential pressure-inducing fans or similar device 105 may be deployed proximate ingress port 106 and be capable of operation in variable airflow pressure rates that induce higher or lower airflow of ambient air into ozone generating device 101 via ingress port 106, and at least partly influencing exhaust air stream 111 at correspondingly higher and lower flow rates.

Figure 2:
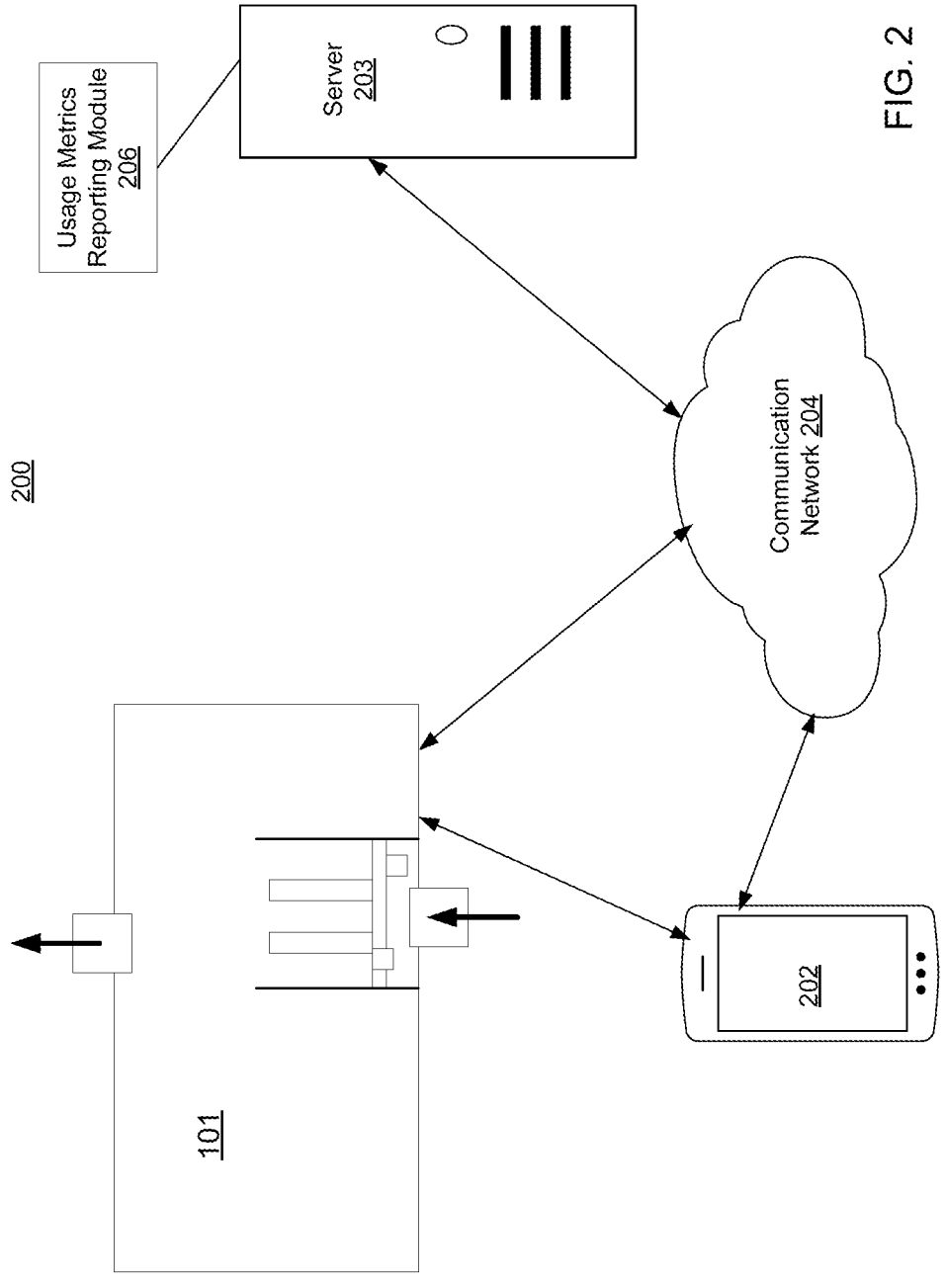
FIG. 2 illustrates, in an example embodiment, an ozone gas generating system including an ozone gas generating device.

FIG. 2 illustrates, in an example embodiment, ozone generating system 200 including ozone generating device 101. In related embodiments, it is contemplated that a group, or cohort, of ozone gas generating devices 101a . . . n (not shown) may be deployed within a given spatial area, wherein "n" is an integer number greater than 1, designating any number of additional ozone gas generating devices. Ozone generating device 101 is communicatively coupled with mobile device 202 which may be such as a mobile phone or tablet computing device. Ozone generating device 101 may also be communicatively coupled, in a cloud-based system as depicted, with server computing device 203 via communication network 204 which can, in some embodiments, be an internet or similar wide area or telecommunication-based connection. In embodiments, mobile device 202 can be communicatively linked to ozone generating device 101 via wireless communication protocols including, but not limited to, Bluetooth, Wi-Fi, LoRa or RFID. In some embodiments, mobile phone device 102 may include a software application that enables communication, either directly via wireless communication or via cloud-based system 200 via communication network 204, with ozone gas generating device 101 in order to set or apply desired threshold values or acceptable ranges of ozone gas concentration, for instance as sensed by local ozone gas concentration sensor device 108. In related embodiments, it is further contemplated that the cohort of ozone gas generating devices 101a . . . *n* as deployed can be communicatively coupled with corresponding ones of mobile devices 202a . . . *n* (not shown).

In some embodiments, usage metrics and reporting module 206 of server 203 within system 200 can acquire data, during or subsequent to a usage session, from controller module 103 of ozone generating device 101. For instance, data transmissions from controller module 103 of ozone generating device 101, can include such as, but not limited to, one or more of user or device account information, geo-location information, timestamp information, recent and accumulated historical ozone gas generation metrics during deployment, for example. In embodiments, server 203 can be maintained at a remotely located provider service or monitoring authority that is communicatively accessible via communications network 204. It is contemplated that, in some variations, at least part of the usage metrics and reporting functionality attributed to usage metrics and reporting module 206 of server computing device 203 as described herein can be deployed by way of a software application stored in a memory of mobile computing device 202 for execution thereon. In some embodiments, mobile computing device 202 can communicatively access server 203 via communication network 204.

FIG. 3 illustrates, in an embodiment, example architecture 300 of controller module 103 of ozone generating device 101 as deployed within ozone generating system 200. Controller module 103, in embodiments, may include processor 301, memory 302 and be interconnected with UV irradiation lamp(s) 102, power source DC battery 304 which may be for instance a low power DC battery or similar power source operating in a range between 1.2V and 20V, and communication interface 307 that is communicatively coupled with communication network 204. Processor 301 can be implemented in an application specific integrated circuit (ASIC) device or field programmable gate array (FPGA) device, in some embodiments. Memory 302 may be such as, but not limited to, a random-access memory. Controller module 103 can also be coupled with ozone gas concentration sensor devices, including local ozone gas concentration sensor device 305 this is positioned within housing 109 and remote ozone gas concentration sensor device 305 that is positioned remotely, and external, from housing 109, such as in a room within which ozone generating device 101 is located and deployed. In embodiments, controller module 103 can also be coupled with remote motion sensor device(s) 309 to detect human presence, as inferred from motion, or lack thereof, with the area surrounding ozone generating device 101. Remote ozone gas concentration sensor devices 305 and remote motion sensor device(s) 309 may be communicatively coupled with controller module 103 via wireless communication employing Wi-Fi or similar wireless communication protocols as described herein, configured in a cloud-connected network of sensors 309, 305 with ozone gas generating devices 101a . . . *n* and server computing device 203. In some embodiments, the cloud connected scheme can be implemented via a cloud-based server computing device 203, with individual ozone gas generating devices 101a . . . *n* considered as respective Internet of Things (IoT) nodes within a given ad hoc network arranged in a mesh or a star network configuration.

Controller module 103 may also include capability for communicatively accessing wireless communication signals, including but not limited to any of Bluetooth, Wi-Fi, LoRa, RFID, and global positioning system (GPS) signals, and incorporate communication interface 307 for communicatively coupling to communication network 104, such as by sending and receiving data transmissions. Controller module 103, in some embodiments, can also incorporate GPS position location functionality based on GPS receiver and transmitter circuitry for accessing and enabling transmission of operational metrics associated with deployment of ozone generating device 101 such as, but not limited to, account information associated with ozone generating device 101, location information, timestamp information and ozone gas operational data associated with ozone generating device 101. Controller module 103 can be communicatively coupled with variable air flow generating device (s) 309, which in embodiments may be airflow pressure differential pressure-inducing fans or devices 105 as described in regard to FIG. 1.

Ozone generator logic module 310 of controller module 103, in embodiments, can be constituted of computer processor-executable code stored in memory 302 that are executable in processor 301, to accomplish ozone gas generation functionality as described herein, associated with usage or deployment of ozone generating device 101. In one embodiment, the software instructions or programs, including any updates thereof, constituting ozone generator logic module 310 can be downloaded to memory 202 by accessing and downloading, via communication network 204, from a remote server computing device, including from server 203, or from mobile computing device 202 via wireless communication protocols as described herein.

Ozone generator logic module 310 of controller module 103, in embodiments, enables deployment of ozone gas generator 101 within ozone gas generating system 200 and includes, in non-transitory memory 302, logic instructions that are executable in processor 301. The instructions when executed by processor 301 cause the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air, the UV irradiation provided via an optical lamp module powered by a direct current (DC) battery source, producing a modified air stream in accordance with the generating and exhausting the modified air stream, the modified air stream having a higher concentration of ozone gas as compared with a trace concentration of ozone gas that is constituted in the incoming stream of ambient air via ingress port 106.

Ozone generator logic module 310 of controller module 103, in some embodiments, also includes, in non-transitory memory 302, logic instructions that are executable in processor 301 to adjust the rate of generating ozone gas based on local and remote sensors 305, 306, and also based on remote motion sensor 308. In embodiments, a plurality of motion sensors 308, or occupancy sensors, can be deployed within the spatial area, and being communicatively coupled to server computing device 203 and to ozone gas generating sensors 101a . . . *n*. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. In embodiments, remote motion sensor 308 may be a proximity-based sensor or may comprise similar sensors deployed to detect or infer presence or absence of living occupants within the spatial area or surroundings. For example, besides a motion sensor, ultrasonic sensors that detect shifts or changes in sound waves that might be associated with presence of living occupants may be deployed to infer presence, or absence, of living occupants within a given space around ozone gas generating device 101. Infrared radiation sensors that detect heat generated from the living occupants can also be deployed to infer presence, or absence, of living occupants within a given space around ozone gas generating device 101. Camera imaging could be deployed, in some embodiments, to detect or infer presence or absence of living occupants. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 50 parts per billion (ppb) and 100 ppb, though it is contemplated that other ranges or values can be implemented.

In some embodiments, when the higher order or "turbocharged" mode is being deployed, one or more of ozone gas generating devices 101*a* . . . *n*, or server computing device 203, may initiate a warning or alert, that it would be unsafe for an individual to enter the spatial area. For example, in an embodiment where the spatial area is a hotel room, flashing LED alert lights may warn an incomer attempting to enter the room that it would be unsafe to enter the room. In some variations, the warning could further advance to initiate a lockout state of the hotel room via existing door locks, to where an incomer would not be able to enter the room or similar enclosed area while one or more of ozone gas generating devices 101*a* . . . *n* are operating in the "turbocharged" mode. Associated with the warning or alert, which in one embodiment, may be a "cleaning in progress—do not enter" message displayed to the incomer attempting to enter the room. In related embodiments, the warning or alert could also include a smoke alarm or piezo-based buzzer already deployed within the hotel room, via existing wireless communication, including via WiFi connectivity. In additional embodiments, a cloud-based alarm system, including but not limited to a smoke or fire alarm) may be triggered by the server computing device 203, if an unsafe ozone condition higher than a threshold ozone gas concentration, is detected.

FIG. 4 illustrates, in an example embodiment, method of operation 400 of ozone generating device 101. Examples of method steps described herein are related to deployment and use of ozone generating device 101 as described herein. According to one embodiment, the techniques are performed in processor 301 executing one or more sequences of software logic instructions that constitute ozone generator logic module 310 of controller module 103. In embodiments, instructions constituting ozone generator logic module 310 may be read into memory 302 from machine-readable medium, such as memory storage devices. Executing the instructions of ozone generator logic module 310 stored in memory 302 causes processor 301 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 410, receiving a stream of ambient air that includes gaseous oxygen via an ingress port within a housing of an ozone generating device.

At step 420, generating ozone gas in accordance with applying ultraviolet (UV) irradiation provided in a wavelength of 185 nanometer (nm) to at least a portion of the gaseous oxygen of the stream of ambient air, the UV irradiation provided via an optical lamp module powered by a direct current (DC) battery source. The shorter 185 nanometers wavelength of UV irradiation generates ozone by reacting with oxygen in the ambient air stream to break it into atomic oxygen, making available a highly unstable oxygen atom that then combines with oxygen in the ambient air stream to form ozone.

At step 430, producing a modified air stream in accordance with the generating. In some embodiments, either one of local ozone gas sensor device 305 or remote ozone gas sensor device 306 can sense ozone concentration being produced by ozone generator device 101, and if the sensed ozone gas concentration level is higher than a predetermined threshold level, processor 301 can operate optical lamp module 102 using an intermittent, duty cycle-based, on/off powered pattern that moderates ozone gas generation into a more acceptable range, and then to maintain it within that range. In some example embodiments, between 50-500 ppb may be predetermined as such an acceptable range, though other ppb values may be deployed. In embodiments, the threshold levels deemed acceptable can be set, or changed from a pre-existing value or values via mobile phone device 202.

At step 440, exhausting the modified air stream via an exhaust port of the housing, the modified air stream having a higher concentration of ozone gas as compared with a trace concentration of ozone gas that is constituted in the stream of ambient air.

In yet another variation, the method can include transmitting, to a computing device such as a remote server computing device, one or more of account information, location information and timestamp information associated with ozone generator device 101 and details of its operation within ozone gas generating system 200.

FIG. 5 illustrates, in yet another example embodiment, a further method of operation 500 of ozone generating device 101. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space as determined in accordance with remote motion sensor device 308, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 5 parts per billion (ppb) and 1,000 ppb. However, it is contemplated that other ranges or values can be deployed; for instance, in a range from 50 ppb to 500 ppb of ozone gas concentration.

At step 510, detecting, via one or more remote sensor devices 306, a condition that is external to the housing. In one embodiment, the condition external to the housing can be determined as being an absence of a person within a predetermined area around the housing, using one or more remote motion sensor device(s) 308.

In a further variation, using one or more remote ozone gas concentration sensor device(s) 306, the condition external to the housing can be determined as a concentration of ozone gas being below a predetermined threshold concentration, for instance in a range of 50 to 500 ppb, within a predetermined area around the housing of ozone gas generating device 101.

At step 520, switching, responsive to the detecting, to a second mode of operation that produces a second modified airstream, the second modified airstream comprising at least one of: (i) a higher concentration of ozone gas than the first modified airstream, and (ii) a higher flowrate of the exhausting as compared with the first modified airstream. In this manner, a higher rate of production of ozone gas can be generated within a given time period and subsequently disseminated into the surroundings. In one embodiment having a heightened safety protocol, remote motion sensor device 308 can be used to detect that no human person(s) are active or occupying the surroundings, such as an enclosed room in which gas generating device 101 is located, before switching to the second mode of operation having increased rate of generation or production of ozone gas.

In an embodiment, the optical lamp module includes one or more optical lamps, and the second mode of operation comprises activating at least one additional optical lamp of the optical lamp module.

In another variation, the higher flowrate of the second modified air stream is accomplished in accordance with varying an operational state of one or more pressure differential-inducing devices disposed at least partially within the housing. Such varying of operational state can be accomplished by activating additional fans, speeding up deployed fans, or any combination thereof, whereupon additional fans and/or fans operating at higher speeds accomplish higher ozone generation rates, and faster times to reach a given concentration of ozone gas, in accordance with the higher order, or "turbocharged", mode as described herein.

In yet another embodiment, the method includes terminating at least the second mode of operation, responsive to detecting that a concentration of ozone gas exceeds a predetermined threshold concentration in ppb in an area around the housing.

Figure 6:
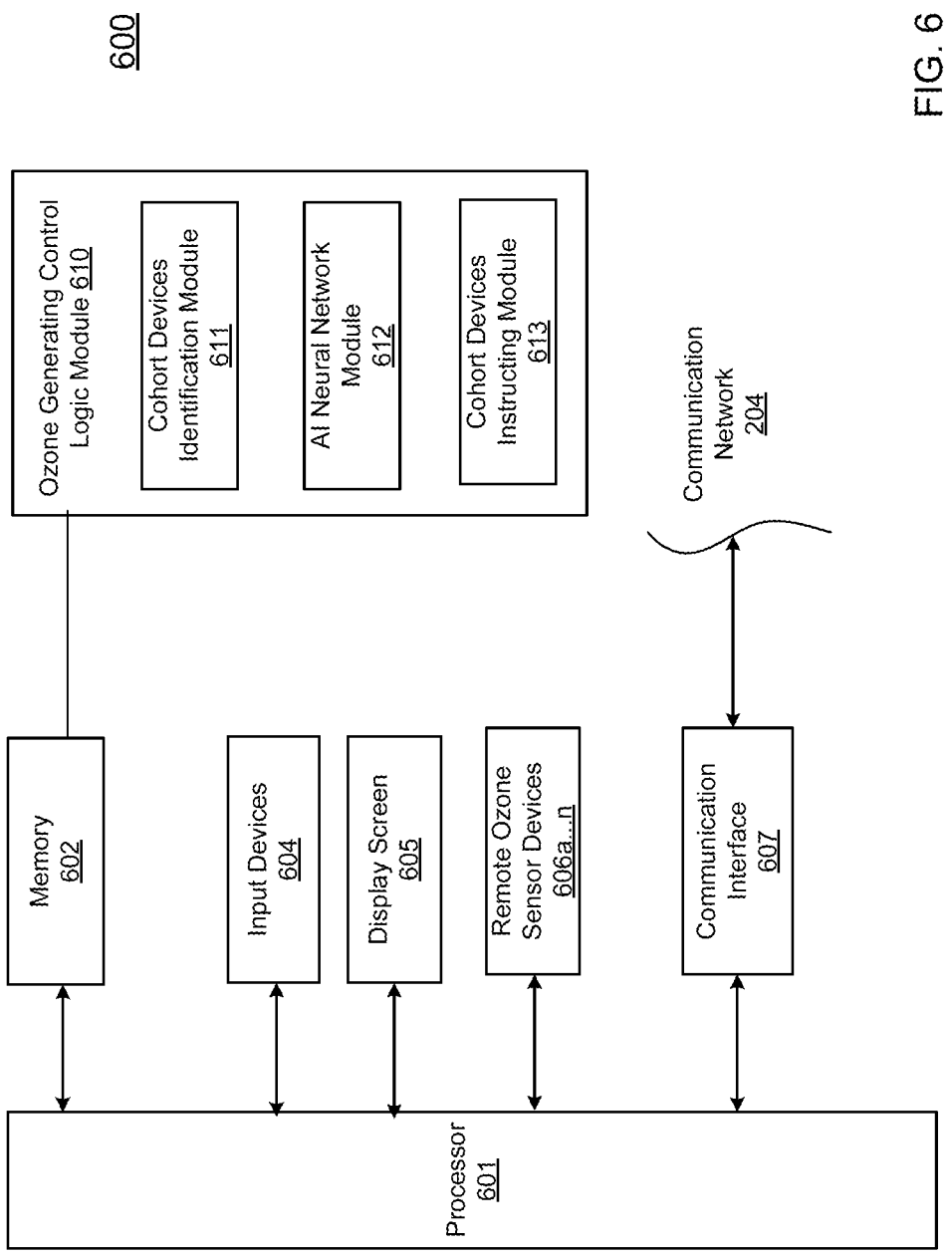
FIG. 6 illustrates, in an example embodiment, a computing device architecture incorporating an artificial intelligence machine learning-based system for controlling a cohort of ozone gas generating devices.

FIG. 6 illustrates, in an example embodiment, computing device architecture 600 incorporating an artificial intelligence machine learning-based system for controlling a cohort of ozone gas generating devices 101*a* . . . *n*. The term cohort, as referred to herein, refers to a group of ozone gas generating devices deployed within a given spatial area for the common, or individual, purpose of generating ozone gas within ambient air of that spatial area. The spatial area may be a room, a hall, an enclosed or partially enclosed area, and can defined in terms of location coordinates, either in local or global (x,y) coordinates that define a boundary or perimeter enclosing the spatial area.

Server computing device 203, in a cloud-based embodiment, includes processor 601, memory 602, display screen 603, input mechanisms 604 such as a keyboard or software-implemented touchscreen input functionality, and communication interface 607 for communicating via communication network 204. Remote ozone sensor devices 606*a* . . . *n* are physically located in the spatial area associated with the cohort of ozone gas generating devices 101*a* . . . *n*, but are communicatively interfaced with processor 601 of server computing device 203 via wireless communication using communication network 204 and communication interface 607. Memory 602 may comprise any type of non-transitory system memory, storing instructions that are executable in processor 601, including such as a static random access memory (SRAM), dynamic random access memory (DRAM), synchronous DRAM (SDRAM), read-only memory (ROM), or any combination thereof.

Ozone generating control logic module 610 includes processor-executable instructions stored in memory 602 of server computing device 203 in a cloud-based embodiment, the instructions being executable in processor 601. Neural network logic module 105 may comprise portions or sub-modules including cohort devices identification module 611, artificial intelligence (AI) neural network module 612, and cohort devices instructing module 613.

Processor 201 uses executable instructions stored in cohort devices identification module 611 to identify, at server computing device 203 in one embodiment, a plurality of ozone gas generating devices 101*a* . . . *n* that constitute the cohort. Ones of ozone gas generating devices 101*a* . . . *n* that are in operation within a given spatial area may be classified, or assigned, as belonging to a cohort based on their physical locations as sensed by server computing device 203. The spatial area may be designated in accordance with coordinate (x,y) locations or perimeter that is predetermined, such as a room, a hall or similar area. Physical locations of respective ozone gas generating devices 101*a* . . . *n* can be determined or estimated using global positioning system in conjunction with a GPS receiver in the ozone generating devices 101*a* . . . *n*, or also estimated as a location corresponding with a respective one of mobile phones 202*a* . . . *n* in wireless communication therewith. In some embodiments, ozone gas generating devices 101*a* . . . *n* can be in wireless communication, such as but limited to Bluetooth protocol, with a fixed wireless communication access point device within the spatial area, with coordinate (x,y) locations within the spatial area being estimated based on received wireless signal strengths.

Processor 201 uses executable instructions stored in AI, or machine learning, neural network module 612 to detect, via at least one of ozone gas sensor devices 606*a* . . . *n* located in a spatial area associated with the cohort in conjunction with one or more processors of computing device 203, a concentration of ozone gas constituent of ambient air within the spatial area. In embodiments, the concentration of ozone gas constituent of ambient air may be detected based on at least partly upon using a trained machine learning model in conjunction with the plurality of ozone gas sensor devices 606*a* . . . *n*.

The neural network, in one embodiment, is configured with a set of input layers, an output layer, and one or more intermediate layers connecting the input and output layers. In embodiments, the input layers are associated with input features or input attributes that relate to digital ad data, such as, but not limited to, digital ad data sourced, created or accessible via mobile computing device 103. Output attributes generating module 212 can present resultant output attributes at user interfaces including display screen 203 or other display interface devices that enable selection of specific ones of the output attributes generated.

The neural network as trained can be deployed in accordance with the respective ones of set of input layers based at least in part upon adjusting the initial matrix of weights in generating, at the output layer, at least one digital ad output attribute. In some embodiments, the output attribute relates to a benefit or a result that would be a desired outcome from the cohort of ozone gas generating devices 101a . . . n within the spatial area. In embodiments, the adjusting comprises recursively adjusting the initial matrix of weights by backpropagation in generating the output attributes. Generating the output attribute proceeds, based on the recursively adjusting, in accordance with diminishment of an error matrix computed at the output layer of the neural network. In embodiments, the backpropagation comprises a backward propagation of errors in accordance with an error matrix as computed at the output layer, the errors being distributed backwards throughout the weights of the neural network intermediate layers.

In the particular embodiment of a convolution neural network model, the convolution operation typically embodies two parts of inputs: (i) input feature map data, and (ii) a weight, also referred to as output filter, or kernel. Given the input channel data with W (Width)×H (Height)×IC data cube and R×S×IC filter, the output of direct convolution may be formulated as:

$$y_{w,h} = \sum_{r=0}^{R-1}\sum_{s=0}^{S-1}\sum_{c=0}^{C-1} x_{(w+r),(h+s),c} * w_{r,s,c}$$

where:

X=input data/input feature/input feature map
w=width of the input or output data
h=height of the input or output data
R=weight size (width)
S=weight size (height)
C=number of input channels
Y=output data/output feature/output feature map
W=filter/kernel/weight Machine learning inference and training networks typically are configured to include many convolution layers. Typically, the output of one convolution layer becomes the input of the next convolution layer. For each input channel, the filter, or weight, are convoluted with data and generates output data. The same location of data of all the input channels are summed together and generate the output data channel. The weight is applied to detect a particular defect feature or type based on an input data stream of digital parameters.

Each output channel of the convolution model is represented by an output filter or weight used to detect one particular feature or pattern of the input feature data stream. Convolution networks may be constituted of many output filters or weights for each layer of the convolution model corresponding to respective features or patterns in the input attributes data stream.

Although example embodiments herein relate to a convolutional neural network, it is contemplated that other neural network models, including a recurrent neural network model, may be applied, including hybrid models that incorporate aspects of said neural network models.

Processor 201 uses executable instructions stored in cohort devices instructing module 613 to instruct, using processor 601 responsive to detecting the concentration of the ozone gas constituent as being one of above and below a predetermined threshold concentration, at least one ozone gas generating device of the cohort of ozone gas generating devices 101a . . . n to either increase or decrease its rate of ozone gas generation. The instruction, in embodiments, can manifest by processor 601 transmitting one or more encoded commands to one or more of ozone gas generating devices 101a . . . n, for example via communication interface 607 and transmitted over communication network 204.

FIG. 7 illustrates, in an example embodiment, method 700 of controlling a cohort of ozone gas generating devices 101a . . . n that incorporates an artificial intelligence machine learning neural network-based system.

At step 710, identifying, at computing device 203, a plurality of ozone gas generating devices 101a . . . n that constitute the cohort.

At step 720, detecting, via at least one of remote ozone gas sensor devices 606a . . . n located in a spatial area associated with the cohort in conjunction with one or more processors 601 of the computing device 203, a concentration of ozone gas constituent of ambient air within the spatial area.

At step 730, instructing, using the one or more processors 601 responsive to detecting the concentration of the ozone gas constituent as being one of above and below a predetermined threshold concentration, at least one ozone gas generating device of the cohort 101a . . . n to perform one of increasing and decreasing a rate of ozone gas generation associated therewith.

In embodiments, the at least one remote ozone gas sensor device comprises a plurality of remote ozone gas sensor devices 606a . . . n located within the spatial area associated with the cohort, but not necessarily incorporated within ozone gas generating devices 101a . . . n as distinct from local ozone gas concentration sensors 108, and the method further comprises detecting the concentration of ozone gas constituent of ambient air at least partly using a trained machine learning model in conjunction with plurality of ozone gas sensor devices 606a . . . n. In one aspect, the trained machine learning model comprises one of a trained convolutional neural network and a trained recurrent neural network.

In one variation, responsive to the instructing, the at least one ozone gas generating device of the cohort 101a . . . n increases the rate of ozone gas generation associated therewith in accordance with switching from a first mode to a second mode of ozone gas generation, the second mode of ozone gas generation being associated with a higher rate of generation of ozone gas than the first mode.

In one aspect, the at least ozone generating device includes an optical lamp module comprised of a plurality of optical lamps 102, and the second mode of ozone gas generation comprises activating at least one additional optical lamp of the plurality of optical lamps 102.

In yet another aspect, responsive to the instructing, the at least one ozone gas generating device of the cohort 101a . . . n decreases the rate of ozone gas generation associated therewith in accordance with ay least one of (i) switching from the second mode to the first mode of ozone gas generation, and (ii) switching from an operational state to a non-operational state, where the operational state refers to a state of active generation of ozone gas, and the non-operational state may be a power-off or inactive state where no ozone gas is being generated.

In yet another embodiment, the at least one ozone gen-erating device includes an optical lamp module comprised of a plurality of optical lamps 102, and the first mode of ozone gas generation comprises de-activating at least one optical lamp of the plurality of optical lamps 102.

FIG. 8 illustrates, in an example embodiment 800, input datasets 801 and output attribute 802 of an artificial intelli-gence machine learning-based system that includes neural network module 612 for controlling a cohort of ozone gas generating devices 101a . . . n. In one aspect, input datasets 801 comprise one or more of: ozone gas generation capacity in regular mode of operation, ozone gas generation capacity in higher order mode of operation, location coordinates defining external boundaries or perimeter of a given spatial area, coordinate location of ozone gas generating device within the spatial area, model identification of ozone gas generating device, device operational reliability metrics, device wireless communication reliability metrics and device historical, cumulative ozone gas generating metrics. In embodiments, output attribute 802 comprises a desired concentration of ozone gas as constituted in ambient air of the spatial area.

FIG. 9 illustrates, in one embodiment, method 900 of training an artificial intelligence machine learning-based system in controlling a cohort of ozone gas generating devices 101a . . . n. It is contemplated that, in embodiments, the training can embody supervised learning techniques, unsupervised learning techniques, or some combination thereof.

At step 910, receiving a plurality of input datasets at respective ones of a plurality of input layers of a neural network, the neural network being instantiated in the one or more processors and having an output layer interconnected to the plurality of input layers via a set of intermediate layers, each of the plurality of input datasets comprising an input attribute associated with ones of a plurality of ozone gas generating devices, ones of the set of intermediate layers being configured in accordance with an initial matrix of weights.

At step 920, training the neural network in accordance with the respective ones of the plurality of input layers based at least in part upon recursively adjusting the initial matrix of weights by back propagation in generating, at the output layer, an output attribute in accordance with diminishment of an error matrix computed at the output layer of the neural network. In deployment of the neural network as trained, the output attribute, in an embodiment, can be a desired target ozone gas concentration level as constituted in ambient of the given spatial area associated with the training. In this manner, the machine learning network is trained to predict the results of ozone gas concentration in ambient air of a given spatial area having a group of ozone gas generation devices 101a . . . n in operation, using back propagation to update the parameters of the neural network so that it can more accurately perform its prediction. In a particular embodiment, the desired target ozone gas concentration, corresponding to output attribute 802 of the neural network, can be predetermined as 100 ppb, though it is contemplated that other ozone gas concentration levels in a range between 50 ppb and 500 ppb may be implemented.

Supervised learning as used herein refers to methods of training a machine learning (ML) algorithm based on labelled input dataset streams, while guiding the ML algo-rithm model in learning in accordance with expert knowl-edge in ozone gas generation device characteristics applied to provide feedback, whereby the ML algorithm learns the mapping function from the input features to the desired output attribute. Input dataset labels applied via the training can be related to characteristics associated with ozone gas generating devices, such as, for example and without limi-tation, ozone gas generation capacity in regular mode of operation, ozone gas generation capacity in higher order mode of operation, location coordinates defining external boundaries or perimeter of a given spatial area, coordinate location of ozone gas generating device within the spatial area, model identification of ozone gas generating device, device operational reliability metrics, device wireless com-munication reliability metrics and device historical, cumu-lative ozone gas generating metrics.

In unsupervised learning embodiments, clustering tech-niques or algorithms can be applied to find natural groups or clusters in the ozone gas generating device characteristics, interpretive of input data. The unsupervised learning tech-nique, in an embodiment, employs a clustering algorithm that identifies one or more clusters in ozone gas generating device attributes and applies respective dataset labels to the input dataset features.

In embodiments, as the trained neural network is deployed in a production or normal usage environment, the neural network can be subjected to, and undergo, continuous learning and refinement in accuracy as originally trained, and thus benefit from additional, subsequent input datasets acquired during the regular usage in deployment.

Although embodiments are described in detail herein with reference to the accompanying drawings, it is contemplated that the disclosure herein is not limited to only such literal embodiments. As such, many modifications including varia-tions in sequence of the method steps in conjunction with varying combinations of user interface features disclosed herein will be apparent to practitioners skilled in this art. Accordingly, it is intended that the scope of the invention be defined by the following claims and their equivalents. Fur-thermore, it is contemplated that a particular feature described either individually or as part of an embodiment can be combined with other individually described features, or parts of other embodiments. Thus, the absence of describ-ing combinations of such does not preclude the inventor from claiming rights to such combinations.

What is claimed is:

1. A method, performed in one or more processors of a computing device, of controlling a plurality of ozone gas generating devices, the method comprising:

detecting, via at least one remote ozone gas sensor device in communication with the one or more processors, a concentration of ozone gas constituent of ambient air within a spatial area, the plurality of ozone gas gener-ating devices generating ozone gas at a first rate of ozone gas generation, the at least one remote ozone gas sensor device being located in the spatial area; and responsive to detecting the concentration of the ozone gas constituent as being one of above and below a prede-termined threshold concentration, performing, by the plurality of ozone gas generating devices in conjunc-tion with the one or more processors of the computing device, one of increasing and decreasing the first rate of ozone gas generation to a second rate of ozone gas generation.

2. The method of claim 1 wherein the at least one remote ozone gas sensor device comprises a plurality of remote ozone gas sensor devices located within the spatial area associated with the plurality of ozone gas generating devices, and further comprising detecting the concentration of ozone gas constituent of ambient air at least partly using a trained machine learning model in conjunction with the plurality of remote ozone gas sensor devices.

3. The method of claim 2 further comprising producing the trained machine learning model via a training process comprising:

receiving a plurality of input datasets at respective ones of a plurality of input layers of a neural network, the neural network being instantiated in the one or more processors and having an output layer interconnected to the plurality of input layers via a set of intermediate layers, each of the plurality of input datasets comprising an input attribute associated with ones of a plurality of ozone gas generating devices, ones of the set of intermediate layers being configured in accordance with an initial matrix of weights; and training the neural network in accordance with the respective ones of the plurality of input layers based at least in part upon recursively adjusting the initial matrix of weights by back propagation in generating, at the output layer, an output attribute in accordance with diminishment of an error matrix computed at the output layer of the neural network.

4. The method of claim 3 wherein the plurality of input datasets comprise one or more of: ozone gas generation capacity in regular mode of operation, ozone gas generation capacity in higher order mode of operation, location coordinates defining external boundaries or perimeter of a given spatial area, coordinate location of ozone gas generating device within the spatial area, model identification of ozone gas generating device, device operational reliability metrics, device wireless communication reliability metrics and device historical, cumulative ozone gas generating metrics.

5. The method of claim 3 wherein the output attribute comprises a desired concentration of ozone gas as constituted in ambient air of the spatial area.

6. The method of claim 2 wherein the trained machine learning model comprises one of a trained convolutional neural network and a trained recurrent neural network.

7. The method of claim 1 wherein, responsive to the instructing, at least one ozone gas generating device of the plurality of ozone gas generating devices increases the rate of ozone gas generation associated therewith in accordance with switching from a first mode to a second mode of ozone gas generation, the second mode of ozone gas generation being associated with a higher rate of generation of ozone gas than the first mode.

8. The method of claim 7 wherein the at least ozone generating device includes an optical lamp module comprised of a plurality of optical lamps, and the second mode of ozone gas generation comprises activating at least one additional optical lamp of the plurality of optical lamps.

9. The method of claim 7 wherein, responsive to the instructing, the at least one ozone gas generating device of the plurality of ozone gas generating devices decreases the rate of ozone gas generation associated therewith in accordance with one of (i) switching from the second mode to the first mode of ozone gas generation, and (ii) switching from an operational state to a non-operational state.

10. The method of claim 9 wherein the at least ozone generating device includes an optical lamp module comprised of a plurality of optical lamps, and the first mode of ozone gas generation comprises de-activating at least one optical lamp of the plurality of optical lamps.

11. A computing device comprising:

one or more processors; and a non-transitory memory including instructions, the instructions when executed by the one or more processors causing the one or more processors to perform operations comprising:

detecting, via at least one remote ozone gas sensor device in communication with the one or more processors, a concentration of ozone gas constituent of ambient air within a spatial area, the plurality of ozone gas generating devices generating ozone gas at a first rate of ozone gas generation, the at least one remote ozone gas sensor device being located in the spatial area; and responsive to detecting the concentration of the ozone gas constituent as being one of above and below a predetermined threshold concentration, performing, by the plurality of ozone gas generating devices in conjunction with the one or more processors of the computing device, one of increasing and decreasing the first rate of ozone gas generation to a second rate of ozone gas generation.

12. The computing device of claim 11 wherein the at least one remote ozone gas sensor device comprises a plurality of remote ozone gas sensor devices located within the spatial area associated with the plurality of ozone gas generating devices, and further comprising detecting the concentration of ozone gas constituent of ambient air at least partly using a trained machine learning model in conjunction with the plurality of remote ozone gas sensor devices.

13. The computing device of claim 12 further comprising instructions executable in the processor to produce the trained machine learning model via a training process comprising:

receiving a plurality of input datasets at respective ones of a plurality of input layers of a neural network, the neural network being instantiated in the one or more processors and having an output layer interconnected to the plurality of input layers via a set of intermediate layers, each of the plurality of input datasets comprising an input attribute associated with ones of a plurality of ozone gas generating devices, ones of the set of intermediate layers being configured in accordance with an initial matrix of weights; and training the neural network in accordance with the respective ones of the plurality of input layers based at least in part upon recursively adjusting the initial matrix of weights by back propagation in generating, at the output layer, an output attribute in accordance with diminishment of an error matrix computed at the output layer of the neural network.

14. The computing device of claim 13 wherein the plurality of input datasets comprise one or more of: ozone gas generation capacity in regular mode of operation, ozone gas generation capacity in higher order mode of operation, location coordinates defining external boundaries or perimeter of a given spatial area, coordinate location of ozone gas generating device within the spatial area, model identification of ozone gas generating device, device operational reliability metrics, device wireless communication reliability metrics and device historical, cumulative ozone gas generating metrics.

15. The computing device of claim 13 wherein the output attribute comprises a desired concentration of ozone gas as constituted in ambient air of the spatial area.

16. The computing device of claim 12 wherein the trained machine learning model comprises one of a trained convolutional neural network and a trained recurrent neural network.

17. The computing device of claim 11 wherein, responsive to the instructing, at least one ozone gas generating device of the plurality of ozone gas generating devices increases the rate of ozone gas generation associated therewith in accordance with switching from a first mode to a second mode of ozone gas generation, the second mode of ozone gas generation being associated with a higher rate of generation of ozone gas than the first mode.

18. The computing device of claim 17 wherein the at least ozone generating device includes an optical lamp module comprised of a plurality of optical lamps, and the second mode of ozone gas generation comprises activating at least one additional optical lamp of the plurality of optical lamps.

19. The computing device of claim 17 wherein, responsive to the instructing, the at least one ozone gas generating device of the plurality of ozone gas generating devices decreases the rate of ozone gas generation associated therewith in accordance with one of (i) switching from the second mode to the first mode of ozone gas generation, and (ii) switching from an operational state to a non-operational state.

20. The computing device of claim 19 wherein the at least ozone generating device includes an optical lamp module comprised of a plurality of optical lamps, and the first mode of ozone gas generation comprises de-activating at least one optical lamp of the plurality of optical lamps.

\* \* \* \* \*